United States Patent
Turner et al.

(10) Patent No.: US 9,737,627 B2
(45) Date of Patent: Aug. 22, 2017

(54) ENERGIZED AIR FRESHENING APPARATUS COMPRISING PERFUME MIXTURES HAVING AN OLFACTIVE INDEX

(71) Applicant: The Procter & Gamble Company, Cincinnati, OH (US)

(72) Inventors: Ronald David Turner, Walton, KY (US); George Kavin Morgan, Hamilton, OH (US); Zaiyou Liu, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 251 days.

(21) Appl. No.: 14/744,360

(22) Filed: Jun. 19, 2015

(65) Prior Publication Data

US 2016/0367715 A1    Dec. 22, 2016

(51) Int. Cl.
*A61L 9/12*  (2006.01)
*A61L 9/01*  (2006.01)

(52) U.S. Cl.
CPC ............. *A61L 9/122* (2013.01); *A61L 9/01* (2013.01); *A61L 2209/131* (2013.01)

(58) Field of Classification Search
CPC ....... A61L 9/01; A61L 9/122; A61L 2209/131
USPC ..................................................... 239/34–60
See application file for complete search history.

(56) References Cited

U.S. PATENT DOCUMENTS

| | | | |
|---|---|---|---|
| 6,729,552 B1 | 5/2004 | Mcewen et al. | |
| 6,793,149 B2 | 9/2004 | Schramm et al. | |
| 7,223,361 B2 * | 5/2007 | Kvietok | A01M 1/2033 239/326 |
| 7,441,755 B2 | 10/2008 | O'Leary et al. | |
| 7,648,127 B2 | 1/2010 | Cittadino | |
| 7,909,264 B2 | 3/2011 | Dunne et al. | |
| 8,931,711 B2 * | 1/2015 | Gruenbacher | A01M 1/2033 220/501 |
| 2007/0257016 A1 | 11/2007 | Jin et al. | |

(Continued)

FOREIGN PATENT DOCUMENTS

| | | |
|---|---|---|
| CA | 2007854 A1 | 3/1991 |
| EP | 253640 A2 | 1/1988 |
| EP | 0 672 425 A1 | 9/1995 |

(Continued)

OTHER PUBLICATIONS

U.S. Appl. No. 14/744,350, filed Jun. 19, 2015, George Kavin Morgan, et al.

(Continued)

*Primary Examiner* — Arthur O Hall
*Assistant Examiner* — Steven M Cernoch
(74) *Attorney, Agent, or Firm* — Abbey A. Lopez; Amy I. Ahn-Roll (57) ABSTRACT

An energized air freshening apparatuses comprising perfume mixtures having an olfactive index and vapor pressure distribution for improved diffusion into a space methods thereof are provided. The energized air freshening apparatus may include a delivery engine containing the volatile perfume mixture, a fluid transport member, and an evaporation assistance element such as a fan that is configured to move a volume of air over the fluid transport member to facilitate evaporation of the perfume mixture into the atmosphere.

18 Claims, 3 Drawing Sheets

(56) References Cited

U.S. PATENT DOCUMENTS

2010/0028289 A1    2/2010  Diersing
2016/0091470 A1*  3/2016  Gafsou .............. G01N 33/0001
                                                             73/23.34

FOREIGN PATENT DOCUMENTS

| EP | 1849485 A1 | 10/2007 |
|----|----|----|
| WO | WO 97/25662 A1 | 7/1997 |
| WO | WO98/58684 A1 | 12/1998 |
| WO | WO03/086488 A1 | 10/2003 |
| WO | WO2005/000018 A1 | 1/2005 |
| WO | WO 2008/100411 A1 | 8/2008 |
| WO | WO2011/106889 A1 | 9/2011 |
| WO | WO2012/107527 A1 | 8/2012 |
| WO | WO 2014/195689 A1 | 12/2014 |
| WO | WO 2014/201339 A1 | 12/2014 |

OTHER PUBLICATIONS

PCT Search Report PCT/US2016/036312; dtd Aug. 17, 2016; 11 Pages.
PCT Search Report PCT/US2016/036309; dtd Jul. 26, 2016; 16 Pages.
All Office Actions P&G Case 13649 U.S. Appl. No. 14/744,350.

* cited by examiner

Fig. 1

ENERGIZED AIR FRESHENING APPARATUS COMPRISING PERFUME MIXTURES HAVING AN OLFACTIVE INDEX

FIELD

The present invention relates to energized air freshening apparatuses comprising perfume mixtures having an olfactive index and vapor pressure distribution for improved diffusion into a space and methods thereof.

BACKGROUND

Various devices in the marketplace provide emission of a volatile perfume mixture over a period of time using a diffusion assistance means, such as heating elements, piezoelectric elements, and motorized fans. While energized assistance of such devices facilitates diffusing the perfume mixture, often times, this leads to quicker perfume mixture end-of-life and/or a less consumer desirable scent experience with high initial scent intensity. Approaches to lengthen the duration of emission of the perfume mixture include formulating less volatile (i.e. lower vapor pressure) perfume materials in the perfume mixture and using a larger volume of the perfume mixture in the device. However, these approaches may not achieve a consumer acceptable scent experience and may involve higher costs for the increased amount of perfume mixture and/or the increased amount of perfume raw materials that are formulated into the perfume mixture.

There remains a need for improved devices that emit volatile perfume mixtures into the atmosphere with consumer desirable scent experiences and longevity, while minimizing the amount of perfume mixture and perfume raw materials necessary to achieve such experience and longevity.

SUMMARY

According to one embodiment, there is provided an apparatus comprising: an evaporation assistance means; a delivery engine positioned within said housing and downstream of said fan assembly, wherein said delivery engine comprises: a reservoir containing a perfume mixture comprising an olfactive index ("OI") of at least about 12,000, wherein said perfume mixture comprises at least about 5 wt. % of perfume raw materials having an odor detection threshold ("ODT") less than or equal to about 1 ppb, and said perfume mixtures comprises about 45 wt. % to about 85 wt. % of perfume raw materials having a weighted average VP range from about 15,000 ppb to about 20,000 ppb; and a fluid transport member; wherein said evaporation assistance means is configured to move a volume of air at least partially over said fluid transport member to evaporate said liquid volatile perfume mixture into the atmosphere.

According to another embodiment, there is provided a method of diffusing a perfume mixture into the atmosphere comprising the step of providing the apparatus of the present invention.

BRIEF DESCRIPTION OF DRAWINGS

The above-mentioned and other features and advantages of the present disclosure, and the manner of attaining them, will become more apparent and the present disclosure itself will be better understood by reference to the following description of various embodiments of the present disclosure taken in conjunction with the accompanying drawings, wherein.

DETAILED DESCRIPTION

"Energized" as used herein refers to an apparatus or system that operates by using an electrical energy source, such as a battery or electrical wall outlet, to diffuse or emit a targeted active such as a perfume mixture.

It should also be understood that when the perfume mixture is described herein as being "delivered" or "emitted" or "diffused", this refers to the volatilization of the volatile component therein, and does not require that the non-volatile components therein be emitted.

The features illustrated or described in connection with one example embodiment can be combined with the features of other example embodiments. Such modifications and variations are intended to be included within the scope of the present disclosure.

For example, the perfume mixture may be contained in a reservoir having a fluid transport member for use with an energized device. An exemplary energized device may be an electrical heating device. More particularly, the device may be an electrical wall plug air freshener having a wick as described in U.S. Pat. No. 7,223,361; a battery powered heating device; or other heating devices (e.g. devices powered by chemical reactions such as catalyst fuel systems; solar powered devices, etc.). In such devices, the wick may be placed next to the heating surface to diffuse the volatile material. The perfume mixture may also be contained in a reservoir for use with an air purifying system or a fan-based air freshener to deliver volatile materials to the atmosphere.

The perfume mixture of the present invention delivers a volatile material in a substantially continuous manner when the device is activated. The emission level of volatile materials may exhibit a uniform intensity until substantially all the volatile materials are exhausted. The continuous emission of the volatile materials can be of any suitable length, including up to: 20 days, 30 days, 60 days, or longer periods.

Perfume Mixture

The perfume mixture of the present invention may comprise at least one perfume raw material ("PRM"). Most conventional PRMs are volatile essential oils. The PRM can be a volatile organic compound commonly available from perfumery suppliers. Furthermore, the PRM can be synthetically or naturally formed materials. Examples include oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like.

While not wishing to be bound by theory, the continuous delivery of a PRM may be a function of various factors. These factors include the physical properties of a PRM such as molecular weight and saturation vapor pressure ("VP"), odor detection threshold ("ODT"), etc.; the type of fluid transport member (e.g. pore size, surface area, etc.) used to diffuse the PRM; environmental factors such as heat, air flow, etc.; the existence of the viscosity and/or surface tension of the perfume mixture containing the PRM; etc.

It has surprisingly been found that the combination of certain VPs and ODTs have an olfative index ("OI") that not only provides consumer desirable scent intensity and longevity, but also consumer desirable scent character. The perfume mixture of the present invention may have an OI of greater than about 12,000, or greater than about 20,000, or greater than about 25,000, or greater than about 28,000, or from about 12,000 to about 500,000, or from about 20,000 to about 100,000, or from about 25,000 to about 100,000, or from about 25,000 to about 80,000, or from about 25,000 to about 60,000, or from about 40,000 to about 60,000.

OI is calculated by the following equation:

$$OI = \sum_i \frac{x_i \cdot P_{vap,i}^{sat,25C}}{ODT_i}$$

where OI is defined as an olfative index of a given perfume composition; $P_{vap,i}^{sat,25C}$ is the VP of a volatile $PRM_i$ at 25° C. expressed in units of ppb; $x_i$ is the molar percent of $PRM_i$ in the perfume composition; and $ODT_i$ is the odor detection threshold of $PRM_i$ expressed in units of ppb; and where all PRMs in the perfume composition are included in the calculated OI value.

VP of individual PRMs can be calculated using the Advanced Chemistry Development Labs ("ACD") (Toronto, Canada) VP computational model, version 14.02 providing VP values at 25° C. expressed in units of torr, and then converted to partial pressure expressed as ppb, based directly on the molecular structure.

ODT of individual PRMs can be calculated using the test method outlined herein, based directly on the molecular structure of the given PRM, and expressed in units of ppb. The OI calculation can be used in selecting PRMs for perfume mixtures for use, for example, in energized air fresheners.

Generation of Molecular Descriptors

For each PRM in a perfume mixture or composition, its molecular structure is used to compute various molecular descriptors. The molecular structure is determined by the graphic molecular structure representations provided by the Chemical Abstract Service ("CAS"), a division of the American Chemical Society, Columbus, Ohio, U.S.A. These molecular structures may be obtained from the CAS Chemical Registry System database by looking up the index name or CAS number of each PRM. For PRMs, which at the time of their testing are not yet listed in the CAS Chemical Registry System database, other databases or information sources may be used to determine their structures. For a PRM which has potentially more than one isomer present, the molecular descriptor computations are conducted using the molecular structure of only one of the isomers, which is selected to represent that PRM. The selection of isomer is determined by the relative amount of extension in the molecular structures of the isomers. Of all the isomers of a given PRM, it is the isomer whose molecular structure has the most extended configuration which is the one that is selected to represent that PRM. The structures for other potential isomers of that PRM are excluded from the computations. The molecular structure of the isomer with the most-extended configuration is paired with the molar % concentration of that PRM, where the molar % reflects the presence of all the isomers of that PRM that are present.

A molecule editor or molecular sketching software program, such as ChemDraw (CambridgeSoft/PerkinElmer Inc., Waltham, Mass., U.S.A.), is used to duplicate the 2-dimensional molecular structure representing each PRM. Molecular structures should be represented as neutral species (quaternary nitrogen atoms are allowed) with no disconnected fragments (e.g., single structures with no counter ions). The winMolconn program described below can convert any deprotonated functional groups to the neutral form by adding the appropriate number of hydrogen atoms and will discard the counter ion.

For each PRM, the molecular sketching software is used to generate a file which describes the molecular structure of the PRM. The file(s) describing the molecular structures of the PRMs is subsequently submitted to the computer software program winMolconn, version 1.0.1.3 (Hall Associates Consulting, Quincy, Mass., U.S.A., www.molconn.com), in order to derive various molecular descriptors for each PRM. As such, it is the winMolconn software program which dictates the structure notations and file formats that are acceptable options. These options include either a MACCS SDF formatted file (i.e., a Structure-Data File); or a Simplified Molecular Input Line Entry Specification (i.e., a SMILES string structure line notation) which is commonly used within a simple text file, often with a ".smi" or ".txt" file name extension. The SDF file represents each molecular structure in the format of a multi-line record, while the syntax for a SMILES structure is a single line of text with no white space. A structure name or identifier can be added to the SMILES string by including it on the same line following the SMILES string and separated by a space, e.g.:
    Cl=CC=CC=Cl benzene.

The winMolconn software program is used to generate numerous molecular descriptors for each PRM, which are then output in a table format. Specific molecular descriptors derived by winMolconn are subsequently used as inputs (i.e., as variable terms in mathematical equations) for the ODT model test method in order to calculate the ODT value for each PRM. The molecular descriptor labels used in the ODT model test method computations are the same labels reported by the winMolconn program, and their descriptions and definitions can be found listed in the winMolconn documentation. The following is a generic description of how to execute the winMolconn software program and generate the required molecular structure descriptors for each PRM in a composition.

Computing Molecular Structure Descriptors using winMolconn:

1) Assemble the molecular structure for one or more perfume ingredients in the form of a MACCS Structure-Data File, also called an SDF file, or as a SMILES file.

2) Using version 1.0.1.3 of the winMolconn program, running on an appropriate computer, compute the full complement of molecular descriptors that are available from the program, using the SDF or SMILES file described above as input.
   a. The output of winMolconn is in the form of an ASCII text file, typically space delimited, containing the structure identifiers in the first column and respective molecular descriptors in the remaining columns for each structure in the input file.

3) Parse the text file into columns using a spreadsheet software program or some other appropriate technique. The molecular descriptor labels are found on the first row of the resulting table.

4) Find and extract the descriptor columns, identified by the molecular descriptor label, corresponding to the inputs required for each model.
   a. Note that the winMolconn molecular descriptor labels are case-sensitive.

Test Method for Determining ODT

The ODT value is computed for each free PRM identified in the perfume mixture through the use of the computational ODT model provided herein written in the Java programming computer language. The program source code for the ODT model is provided herein as two parts, for ODTNeuralNetworks.java and ODTNeuralNetworksDescriptors.java, in word processor text format. Both Java classes are needed to execute the model. The ODTNeuralNetworksDescriptors class is a data container whose purpose is to ensure that molecular descriptors required to execute the neural network are provided to the network in the proper order. The ODTNeuralNetworks class contains the neural network equations, and expects an instance of the ODTNeuralNetworksDescriptors class as input. These two Java source code class files must be combined with other code written by the user, which will add the winMolconn descriptor data required to the ODTNeuralNetworksDescriptors instance, and then pass that object to an instance of ODTNeuralNetworks, and then retrieve the result. These classes expect to be run under the Java software platform version 1.7 or higher (Sun Microsystems/Oracle Corporation, Redwood Shores, Calif., U.S.A.).

Attached herewith is a compact disc having the above-referenced program source code saved as "ODTNeuralNetworks" and "ODTNeuralNetworksDescriptors" ("CD-R"). The word processor text format files were created on Apr. 21, 2015 and contain 141 bytes and 17 bytes of data, respectively. The CD-R is hereby incorporated by reference in its entirety.

The model used to compute ODT values is based on the ODT data provided in the book "Standardized Human Olfactory Thresholds" (Devos, M.; Patte, F.; Rouault, J.; Laffort, P.; Van Gemert, L. J.; Standardized Human Olfactory Thresholds; IRL: Oxford, England, 1990.). In this context, human ODTs are expressed as olfactory power (p.ol) (the negative of the base 10 log of the molar concentration of the odorant in air at which a human first detects the presence of the odorant). These values can be directly transposed to other commonly used units such as ppm (volume) and ppb (volume): thresholds of 1 ppm and 1 ppb are equivalent to p.ol=6 and p.ol=9, respectively. The ODT computational model itself is a set of ten individual computational neural-net ("CNN") models written in the Java programming language. The outputs of all ten CNN models are averaged, and the average p.ol value is reported along with the standard deviation of the set of predicted values.

The starting information required to conduct the ODT computed-value test method which follows, includes the identity and molecular structure of each PRM in the perfume mixture being tested, and the values of various computationally-derived molecular descriptors for each of those PRMs, as determined in accordance with the respective test methods described herein. Additionally, the weight percent of each PRM is also required in order calculate the OI of a perfume mixture.

The specific winMolconn-derived molecular descriptors required for the ODT computation include:
nasS=Count of sulfur atoms;
Hmax=Highest Atom Level HE-State (Site of the most polar hydrogen atom);
fw=Formula weight of the structure;
xc3=$3^{rd}$-order cluster molecular connectivity index;
numHBa=Count of hydrogen-bond accepting atoms;
e2C3O1s=Sum of bond-type electrotopological state indexes for double bonds between an oxygen atom and a carbon atom attached to two other non-hydrogen atoms;
e1C3O1d=Sum of bond-type electrotopological state indexes for single bonds between an hydroxyl oxygen atom and an $sp^2$ carbon atom attached to two other non-hydrogen atoms;
SssCH2=Sum of the electrotopological state index values for methylene (—$CH_2$—) carbon atoms;
xv1=Valence-corrected $1^{st}$-order molecular connectivity index;
SHHBa=Sum of electrotopological state index values for all hydrogen bond accepting atoms in the molecule;
nasO=Count of oxygen atoms;
e2C2O1=Sum of the electrotopological state indexes for double bonds between an oxygen atom and a carbon atom attached to one hydrogen atom and one non-hydrogen atom;
nasC=Count of carbon atoms;
SHHBd=Sum of the hydrogen atom electrotopological state indexes for all hydrogen atoms on hydrogen-bond donating atoms;
nrbond=Count of rotatable bonds;
nelem=Count of element types;
SsCH3=Sum of the electrotopological state indexes for the methyl-group (—$CH_3$) carbon atoms;
eaC2C2a=Sum of bond-type electrotopological state indexes for aromatic bonds between two unsubstituted aromatic carbon atoms;
e1C3O1a=Sum of bond-type electrotopological state indexes for single bonds between a hydroxyl oxygen atom and an aromatic ring carbon atom;
SHCsatu=Sum of the hydrogen atom electrotopological state indexes for hydrogen atoms on $sp^a$ carbons that are also bonded to $sp^2$ carbon atoms;
Qv=Electrotopological state polarity index;
nvx=Count of graph vertices (a count of non-hydrogen atoms).

The specific molecular descriptors are output by the winMolconn software in a table format. The ODT model itself is provided in the ODTNeuralNetworks class. The ODTNeuralNetworksDescriptors helper class provides the setter methods that allow the individual descriptors to be added to the instance of the helper in any order. The getOrderedDescriptors( ) method of the helper class returns the ordered descriptor array required for the neural network model. To execute the ODT model, it is necessary to create a main class that will: 1) create an instance of the of the helper class, 2) populate the instance of the helper class with the required descriptor values from winMolconn, 3) pass ordered descriptor array from the helper class to an instance of the ODT model, 4) and then get the computed ODT value back from the model instance using the getODTModelResult( ) method. The main class is expected to be provided by the user, and is responsible for reading in the winMolconn descriptors, and for reporting the computed ODT value derived from the model for each PRM.

The ODT model is in the form of a CNN. Each CNN is implemented in Java (version 1.7) with each network being embodied in a single Java class object. In order to execute the ODT model, it is necessary to wrap the model class with a Java main class that will create the necessary inputs for the model class, instantiate and execute the class, and then retrieve and report the result. The CNN model class has an associated Descriptor class that is needed to provide the model inputs to the CNN in the proper order. The Java main class should instantiate the respective descriptor class, add the required winMolconn descriptors to the descriptor class instance, and then pass that instance of the descriptor class to the CNN instance as an argument.

Computing the Odor Detection Threshold:
1) Create a Java main executable class that will create and access instances of the ODTNeuralNetworksDescriptors and ODTNeuralNetworks classes provided herein.
2) For each perfume raw material of interest:
   a. Using the winMolconn program (version 1.0.1.3), compute the full complement of available molecular descriptors.
   b. From the output of winMolconn, extract values of the following molecular descriptors: nasS, Hmax, fw, xc3, numHBa, e2C3O1s, e1C3O1d, SssCH2, xv1, SHBa, nasO, e2C2O1, nasC, SHHBd, nrbond, nelem, SsCH3, eaC2C2a, e1C3O1a, SHCsatu, Qv, nvx.
   c. Within a Java main executable program, create an instance of the ODTNeuralNetworksDescriptors class.
   d. Using the setter methods of the ODTNeuralNetworksDescriptors instance, set the values of all of the descriptors listed in step 2b.
   e. Within the same Java main executable program, create an instance of the ODTNeuralNetworks class, using the instance of the ODTNeuralNetworksDescriptors created in step 2d as a parameter argument.
   f. Within the same Java main executable program, retrieve the computed odor detection threshold value for the given perfume raw material by calling the getODTModelResult( ) method on the ODTNeuralNetworks instance created in step 2e.

The perfume mixture may have one of the aforementioned OI ranges and have at least about 5%, by weight of the mixture, of PRMs having an ODT less than or equal to about 1 ppb, or about 10 wt. % of PRMs having an ODT less than or equal to about 1 ppb, or from about 10 wt. % to about 50 wt. % of PRMs having an ODT less than or equal to about 1 ppb, or at least about 20 wt. % of PRMs having an ODT less than or equal to about 1 ppb, or from about 20 wt. % to about 50 wt. % of PRMs having an ODT less than or equal to about 1 ppb, or at least about 30 wt. % of PRMs having an ODT less than or equal to about 1 ppb, or from about 30 wt. % to about 50 wt. % of PRMs having an ODT less than or equal to about 1 ppb, or at least about 10 wt. % of PRMs having an ODT from about 0.5 ppb to about 1 ppb, or from about 10 wt. % to about 50 wt. % of PRMs having an ODT from about 0.5 ppb to about 1 ppb.

Exemplary OI values of perfume mixtures suitable for the present invention are shown in Table 1.

TABLE 1

Calculated OI of Selected Perfume Mixtures

| | OI | Wt. % of PRMs with ODT ≤ 1.0 ppb | Average VP (ppb at 25° C.) | Molar Average ODT |
|---|---|---|---|---|
| Perfume Mixture 1 RA | 60713 | 18.60 | 236842 | 39.3 |
| Perfume Mixture 2 KR | 39813 | 8.42 | 150000 | 68.5 |
| Perfume Mixture 3 LF | 43993 | 13.07 | 117105 | 32.9 |
| Perfume Mixture 4 GS | 52270 | 17.81 | 128947 | 23.6 |
| Perfume Mixture 5 SJ | 26539 | 10.85 | 106579 | 41.7 |
| Perfume Mixture 6 AT | 95753 | 5.57 | 310000 | 26.7 |
| Perfume Mixture 7 FL | 47602 | 5.77 | 170000 | 40.2 |
| Perfume Mixture 8 SM | 12891 | 6.15 | 150000 | 36.2 |
| Perfume Mixture 9 PP | 41375 | 16.48 | 97368 | 25.6 |

The perfume mixture may comprise about 45 wt. % to about 85 wt. % of PRMs having a weighted average VP range from about 15,000 ppb to about 20,000 ppb; or about 50 wt. % to about 80 wt. % of PRMs having a weighted average VP range from about 15,000 ppb to about 20,000 ppb; or about 55 wt. % to about 75 wt. % of PRMs having a weighted average VP range from about 15,000 ppb to about 20,000 ppb. The VP range of an exemplary perfume mixture is shown in Table 2.

TABLE 2

| Wt. % | Average VP (ppb @ 25° C.) | Lo VP (ppb @ 25° C.) | Hi VP (ppb @ 25° C.) |
|---|---|---|---|
| 6.00-10.00 | 131579 | 148684 | >148684 |
| 8.00-12.00 | 98684 | 115132 | 82237 |
| 10.00-14.00 | 65789 | 82237 | 49342 |
| 15.00-19.00 | 32895 | 42763 | 23026 |
| 17.00-21.00 | 13158 | 14868 | 11513 |
| 15.00-19.00 | 9868 | 11513 | 8224 |
| 9.00-13.00 | 6579 | 8224 | 4934 |
| 3.00-7.00 | 3289 | <2303 | 2303 |

Any commercially available PRM may be used in a perfume mixture having the OI range suitable for the present invention. PRMs materials include those listed in Table 3.

TABLE 3

| CAS | PRM | Mol. % | VP (ppb @ 25° C.) | ODT ppb |
|---|---|---|---|---|
| 109-60-4 | PROPYL ACETATE | 0.04 | 47236842 | 575 |
| 470-82-6 | EUCALYPTOL | 0.19 | 2169737 | 19 |
| 68039-49-6 | TRIPLAL | 1.46 | 760526 | 0.6 |
| 13254-34-7 | DIMETOL | 0.30 | 434211 | 88 |
| 6413-10-1 | METHYL DIOXOLAN | 16.54 | 288158 | 56 |
| 78-70-6 | LINALOOL | 2.80 | 119079 | 22 |
| 140-11-4 | BENZYL ACETATE | 14.34 | 215789 | 145 |
| 112-31-2 | ALDEHYDE C-10 | 0.18 | 272368 | 1 |
| 60-12-8 | PHENYL ETHYL ALCOHOL | 5.31 | 97500 | 11 |
| 67634-00-8 | ALLYL AMYL GLYCOLATE | 0.08 | 52632 | 16 |

TABLE 3-continued

| CAS | PRM | Mol. % | VP (ppb@ 25° C.) | ODT ppb |
|---|---|---|---|---|
| 5413-60-5 | CYCLACET | 8.25 | 18026 | 12 |
| 25265-71-8 | DIPROPYLENE GLYCOL | 0.02 | 12947 | 58 |
| 627-93-0 | DIMETHYL ADIPATE | 4.55 | 95395 | 21 |
| 27538-09-6 | ETHYL FRAISON | 0.01 | 15921 | 24 |
| 24851-98-7 | HEDIONE | 1.27 | 934 | 1 |
| 101-86-0 | HEXYL CINNAMIC ALDEHYDE | 1.00 | 917 | 0.2 |
| 77-93-0 | TRIETHYL CITRATE | 0.03 | 230 | 61 |
| 32210-23-4 | VERTENEX | 29.28 | 135526 | 2 |
| 106-24-1 | GERANIOL | 0.93 | 17500 | 0.4 |
| 121-32-4 | ETHYL VANILLIN | 0.13 | 1163 | 0.05 |
| 18479-58-8 | DIHYDRO MYRCENOL | 9.22 | 218421 | 69 |
| 91-64-5 | COUMARIN | 0.20 | 1711 | 0.7 |
| 104-67-6 | UNDECALACTONE/GAMMA | 1.56 | 3566 | 0.4 |
| 104-61-0 | NONALACTONE/GAMMA | 0.92 | 11289 | 2 |
| 28940-11-6 | CALONE 1951 | 0.05 | 1093 | 363 |
| 97-53-0 | EUGENOL | 1.32 | 13684 | 3 |
| 141-13-9 | ADOXAL | 0.02 | 3382 | 10 |
| | Sum | 100 | | |

The perfume mixture may also contain non-volatile components, such as known carrier materials including water, solvents, etc. The perfume mixture may have less than 35%, or less than 25%, by weight the perfume mixture, of solvents that are known in the art.

Perfume mixtures of the present invention may be present in a composition having additional ingredients that are known in the art. For example, the perfume mixture may be combined with carriers, as previously discussed, and/or with malodor ingredients to neutralize odors. Suitable malodor perfume mixtures include cyclodextrin, polyamine polymers, reactive aldehydes and ionones. In such case, the perfume mixture of the present invention may be used in any amount, including 50% to 100%, by weight of the composition, of the perfume mixture and 30% to 50%, by weight of the composition, of one or more carriers; or 0.001% to 10%, by weight of the composition, of the perfume mixture and 90% to 99%, by weight of the composition, of the additional ingredients.

Where the perfume mixture of the present invention is used with a fluid transport member such as a commercially available wick or breathable membrane, the viscosity of the perfume mixture may be considered as it may control how and when the PRM is delivered to the fluid transport member. For example, less viscous PRMs may flow faster than the more viscous PRMs. The more viscous PRM, being slightly less or of similar density with the less viscous phase, may remain in a perfume mixture reservoir via gravity. Thus, the less viscous PRM may be delivered to the transport member and emitted to the atmosphere more quickly. The PRMs may have viscosities less than about 23 cP and surface tension less than about 33 mN/m. In one embodiment, the perfume mixture containing a PRM may have a viscosity of about 1.0 cP to less than about 25 cP, alternatively about 1.0 cP to less than about 23, alternatively about 1.0 cP to less than about 15 cP.

The perfume mixture may be designed such that the perfume mixture may include a surface tension of about 19 mN/m to less than about 33 mN/m, alternatively about 19 mN/m to less than about 30 mN/m, alternatively about 19 mN/m to less than about 27 mN/m.

Apparatus and Method of Diffusing

The present invention includes an apparatus and method of diffusing the perfume mixture described herein into a space. The delivery engine has a liquid volatile perfume mixture therein and a fluid transport member, such as a breathable membrane or wick, in fluid communication with the liquid perfume mixture. The method may comprise the step of providing any air freshening device having an evaporation assistance element and a delivery engine. The evaporation assistance element may be a fan assembly. The method includes activating via a power source the evaporation assistance element. In some embodiments, where the evaporation assistance element includes chemistry or an agitator, the activation step may include adding effective amounts of the chemical evaporation assistance element or manual agitation of the device and/or delivery engine to assist with evaporating the liquid volatile perfume mixture. The method of the present invention also includes activating the evaporation assistance element according to a duty cycle as disclosed herein.

Apparatus

Figure 2:
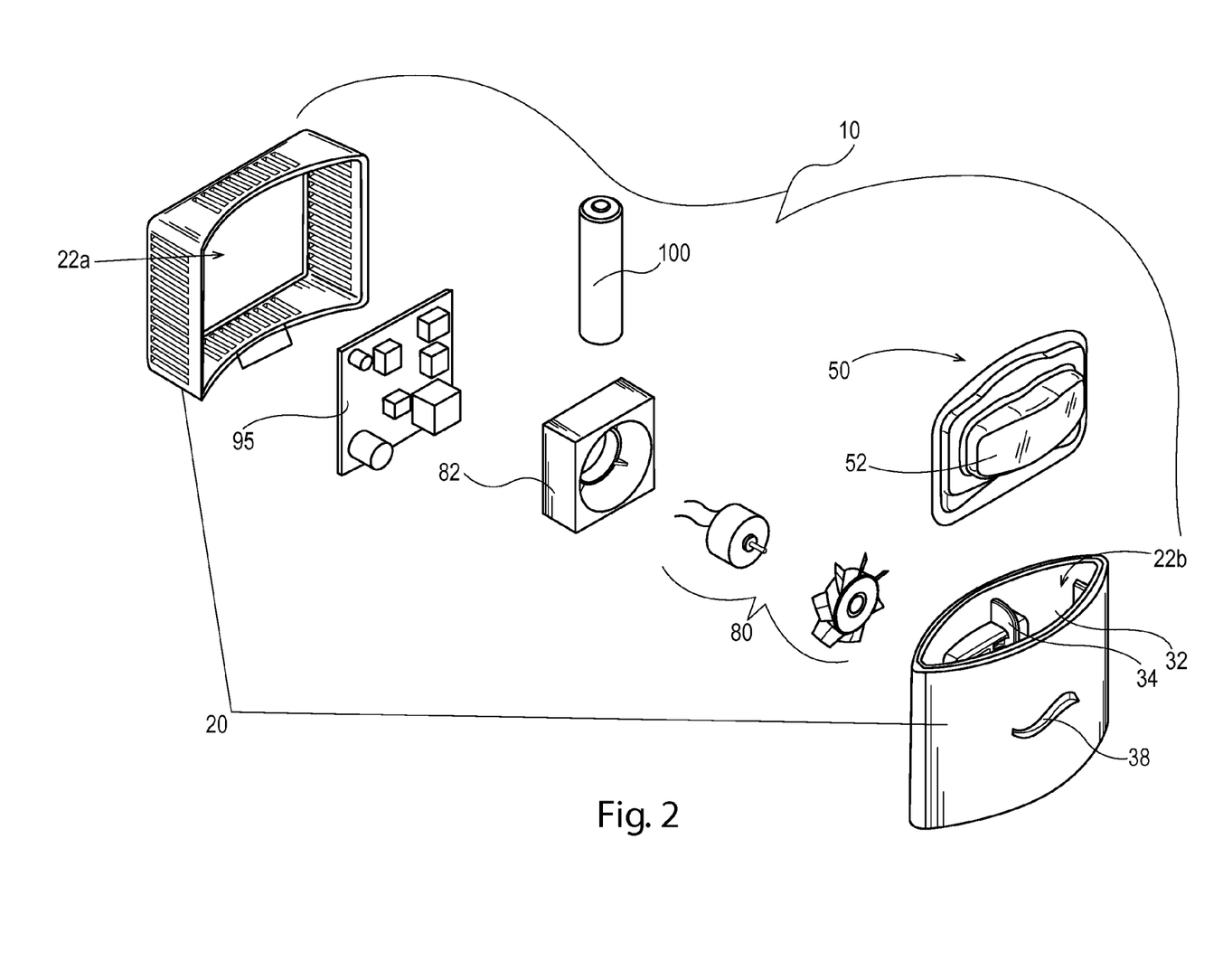
FIG. 2 is an exploded, perspective view of one embodiment of an air freshening apparatus from which a perfume mixture comprising an olfactive index may be diffused.

The perfume mixture of the present invention may be used in any air freshener including energized air fresheners. In some embodiments, the perfume mixture is used in a fan-based air freshener such as that disclosed in U.S. Patent Publication 2014/0369895. The apparatus 10 includes a housing 20 and a delivery engine 50 that contains the perfume mixture and includes a fluid transport member 60, which may include a wick or breathable membrane as shown in FIG. 2.

Figure 3:
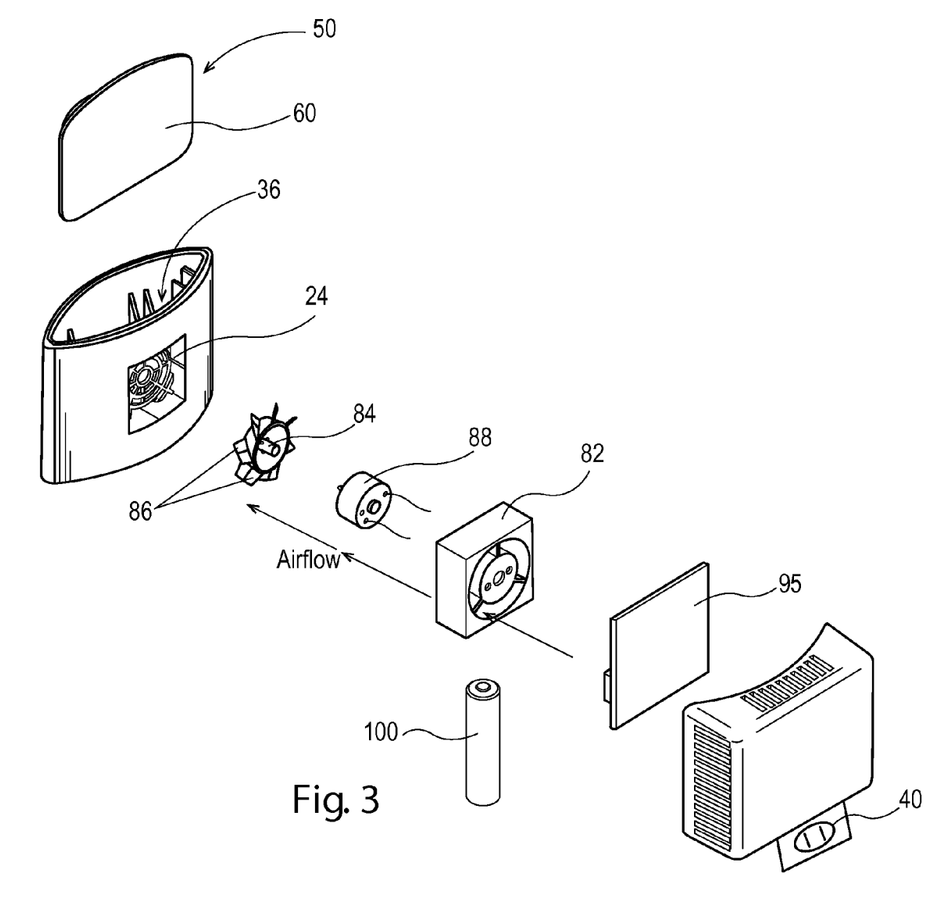
FIG. 3 is an exploded, rear view of the air freshening apparatus shown in FIG. 2.

The housing 20 may house the delivery engine 50 and the fan assembly 80. The housing 20 may be formed from a single part or from multiple parts that are joined together to define at least one chamber 22. The device shown in FIGS. 2 and 3 comprises a two-piece structure that is joined to form a first chamber 22a for housing the fan assembly 80 and a second chamber 22b for housing the delivery engine 50. In some embodiments, the housing 20 defines a single chamber. The first chamber 22a and second chamber 22b are in air flow communication given a fan housing 82 is received by a fan port 24 in the second chamber 22b. Specifically, as shown in FIG. 3, air flows from the fan assembly 80 downstream to the delivery engine 50. "Downstream", as used herein, means a position in an airflow path that is later in time from a referenced position, when measuring air flow through a device.

The housing 20 can comprise at least one projection 34 extending into the housing 20 from the inner wall 32. The at least one projection 34 can comprise pegs, ribs, posts, standoffs, elongate members, and/or pins, for example, which can serve to engage a portion of the delivery engine 50, maintaining the fluid transport member 60 at a distance away from the inner wall 32 of the housing 20. The housing 20 also comprises one or more vents 38 for facilitating the passage of input air and output air into and out of the housing.

The housing 20 is sized such that, when the fan assembly 80 or evaporation assistance element is activated, from about 1 to about 20 air exchanges occur per second, or about 1 to about 10 air exchanges per second or about 5 to about 10 air exchanges per second. Where the fan assembly 80 is programmed to operate 3 minutes in every hour (i.e. 5% duty cycle), for example, and where the fan assembly and housing 20 are configured to provide 10 air exchanges per second, 30 air exchanges may occur per minute during this duty cycle. In some embodiments, the chamber 22 volume ranges from about 2 cc to about 100 cc, or from about 5 cc to about 75 cc or from about 1 cc to about 25 cc.

The delivery engine 50 includes a fluid transport member 60. The fluid transport member 60 may be a microporous membrane, such as that disclosed in U.S. Pat. No. 8,931,711. The fluid transport member 60 is vapor permeable and capable of wicking liquid, yet prevents free flow of liquid out of the fluid transport member, thus addressing leakage problems. The fluid transport member 60 of the present invention may be a microporous membrane with an average pore size of about 0.01 to about 0.06 microns, alternatively from about 0.01 to about 0.05 microns, alternatively about 0.01 to about 0.04 microns, alternatively about 0.01 to about 0.03 microns, alternatively about 0.02 to about 0.04 microns, alternatively about 0.02 microns. The fluid transport member 60 may be filled with any suitable filler and plasticizer known in the art. Fillers may include finely divided silica, clays, zeolites, carbonates, charcoals, and mixtures thereof. Those of ordinary skill in the art will appreciate that the evaporative surface area of the fluid transport member can vary depending on the user preferred size of the delivery engine 50. The evaporative surface area of the fluid transport member 60 may be about 2 $cm^2$ to about 100 $cm^2$, alternatively about 2 $cm^2$ to about 25 $cm^2$, alternatively about 10 $cm^2$ to about 50 $cm^2$. Suitable fluid transport members for the present invention include a microporous, ultra-high molecular weight polyethylene (UHMWPE) optionally filled with silica as described in U.S. Pat. No. 7,498,369. Such UHMWPE fluid transport members include Daramic™ V5, available from Daramic; Solupor®, available from DSM (Netherlands); and Teslin™, available from PPG Industries; and combinations thereof. It is believed that these fluid transport member 60 allows a volatile material to freely dissipate, while containing liquid within the delivery engine 50.

It is contemplated that the delivery engine 50 includes a reservoir 52 and may include two or more reservoirs 52 which can be filled with the same or different perfume mixture. The reservoir 52 may have any configuration that is in fluid communication with the fluid transport member when the delivery engine 50 is activated.

The apparatus 10 may include an evaporation assistance element. While the specification describes the apparatus 10 as including a fan assembly 80, it is contemplated that other evaporation assistance means can be utilized to achieve the evaporation rate of a volatile perfume mixture for the present invention. Such evaporation assistance element may include an agitation member or agitator, both powered agitator and manual agitator, to assist with agitating the liquid volatile perfume mixture in the reservoir. The evaporation assistance element may also include a heating element to heat the liquid volatile perfume mixture, a chemical constituent to speed evaporation or release rates, use of a chemically heated membrane to provide increased evaporation via exothermic reaction, or synergistic combinations thereof.

Where a fan assembly 80 is used, it can comprise any suitable fan or components configured to produce and/or intermittently move a volume of air into the fan inlet 90 and over the fluid transport member 60 of the delivery engine 50. The fan assembly 80 can be housed in a fan housing 82. In various embodiments, the fan assembly 80 can be positioned up to about 18 inches from the microporous membrane 60. The fan assembly 80 may comprises a rotatable hub 84, and at least two fan blades 86 extending from the rotatable hub or otherwise attached to or formed with the rotatable hub, and a motor 88.

A controller 95 may be positioned in electrical communication with a power source 100 and fan 80, such that the controller can instruct the fan 80 when to activate and which speed to rotate to force the volume of air over the microporous membrane 60. While the power source 100 is shown in FIGS. 2 and 3 as a battery, it can be other known sources of power in the art (e.g. solar, wall outlets, etc.). The fan assembly 80 may produce air speeds in the range of about 5 feet per minute to 400 feet per minute or alternatively from about 50 feet per minute to 250 feet per minute; although others air speeds could be possible.

The operation program for the fan assembly 80 may be based on characteristics of the perfume mixture. Perfume mixtures with lower vapor pressures will likely evaporate slower than volatile perfume mixtures with higher vapor pressures. In various embodiments, the fan assembly 80 may not be activated until the fluid transport member 60 has reached full saturation or near full saturation of the volatile perfume mixture. In one embodiment, the deactivation time period of the fan assembly 80 can be related to the time period necessary for the volatile perfume mixture to evaporate and saturate, or at least partially saturate, the space with the vapor phase volatile perfume mixture. The activation time period of the fan assembly 80 is programmed in the microprocessor 95 and can be related to the time period necessary to expel substantially all of the vapor phase volatile perfume mixture from the delivery engine 50 into the atmosphere. Once the vapor has been expelled from the delivery engine 50, the fan assembly 80 can be placed in an inactive state to again allow a portion of the volatile perfume mixture to enter the vapor phase.

By activating the fan assembly 80 for a period of time equal to, or approximately equal to, the amount to time necessary to expel at least most of the vapor phase volatile perfume mixture, the lifetime of the power source can be optimized. Through control of the fan assembly 80, maximum vapor phase volatile perfume mixture release can be achieved with a minimum amount of fan assembly running time. In various embodiments, the sequencing or pattern of activator actuation, or the flow rate of the volume of air produced by the fan assembly 80, can be adjusted to allow full or near full saturation of the volatile perfume mixture within the space for maximizing the vapor phase volatile perfume mixture release. In one embodiment, the fan assembly 80 can be activated for about 1 to about 10 seconds and then deactivated for about 1 to about 10 seconds, for example.

In various embodiments, the duration of activation of the fan assembly 80 or the flow rate of the volume of air provided by the fan assembly can be increased to provide a higher intensity of volatile perfume mixture expulsion from the delivery engine 50. The fan assembly 80 can operate continuously or have intermittent operation. The fan assembly 80 may toggle on and off for a duty cycle of about 5% to about 50%, or from about 8% to about 20%. By providing a period of time between consecutive activations of the fan assembly, a user is more likely to notice a scent of the volatile perfume mixture again and avoid habituation.

The evaporation rate of a liquid perfume mixture from the delivery engine 50 can be about 5 mg/hr to about 75 mg/hr, or about 10 mg/hr to about 75 mg/hr, Or about 15 mg/hr to about 70 mg/hr, or about 25 mg/hr to about 70 mg/hr, or about 25 mg/hr to about 60 mg/hr, or about 25 mg/hr to about 40 mg/hr.

EXAMPLES

Perfume Intensity Test

Perfume mixtures 1 to 9 in Table 1 herein were tested for scent intensity against a Control Mixture, as shown in Table 4.

TABLE 4

| Calculated OI of Control Mixture | | | |
| --- | --- | --- | --- |
| OI | Wt. % having an ODT ≤ 1.0 ppb | Average VP (ppb at 25° C.) | Molar Average ODT (ppb) |
| 18917.62 | 16.31 | 77000 | 20.5 |

Sensory Room Description: large rooms are 15'×15'×8' tall. The rooms have three glass walls, with a glass door on the front-most wall. The back wall is an aluminum panel and the ceiling is likewise aluminum. The floor is industrial grade tile covering. This room construction eliminates perfume absorption into surfaces which is common with typical construction (drywall, linoleum tiles, etc.).

Perfume Intensity Evaluation Procedure
1. The sensory room air controller is set to purge, which removes air from the room to outside the building. This setting is maintained for a period of fifteen minutes.
2. A trained odor evaluator verifies that there is not any residual perfume or room odor present in the room. If residual odor remains in the room, step 1, above, is repeated.
3. Once the room is determined to have no residual odor, the sensory room air controller is then adjusted to two air exchanges per hour, and no auxiliary fan in the room. At this point the room is set to ramp to set points for testing. In this manner, the room temperature and humidity are adjusted to the desired set points for testing, which are room temperature of 70° F. and Humidity of no greater than 40%.
4. After the room has equilibrated to the desired setpoints, an evaluator enters the room and places the test product at the desired location within the room and activates (turns the device on) the device. The evaluator then leaves the room ensuring the door closes behind them (Doors are set to remain closed at all times unless physically opened to enter/exit the room). Trained odor evaluators enter the odor room and close the door.
5. The product remains undisturbed in the room for a period of 60 minutes. At the 1 hour timepoint, trained odor evaluators enter the room and perform perfume odor evaluations over the next sixty seconds, making observations on intensity, character and distribution within the room. All doors are closed upon entering/exiting the room and remain closed during the test period.

Perfume Intensity Scale:
81-100=very strong, i.e., extremely overpowering, permeates into nose, can almost taste it;
61-80=strong, i.e., very room filling, but slightly overpowering;
41-60=moderate, i.e., room filling, character clearly recognizable;
21-40=weak, i.e., can be smelled in all corners, still can recognize character;
1-20=very weak, i.e., cannot smell in all parts of the room;
0=no odor.

Figure 1:
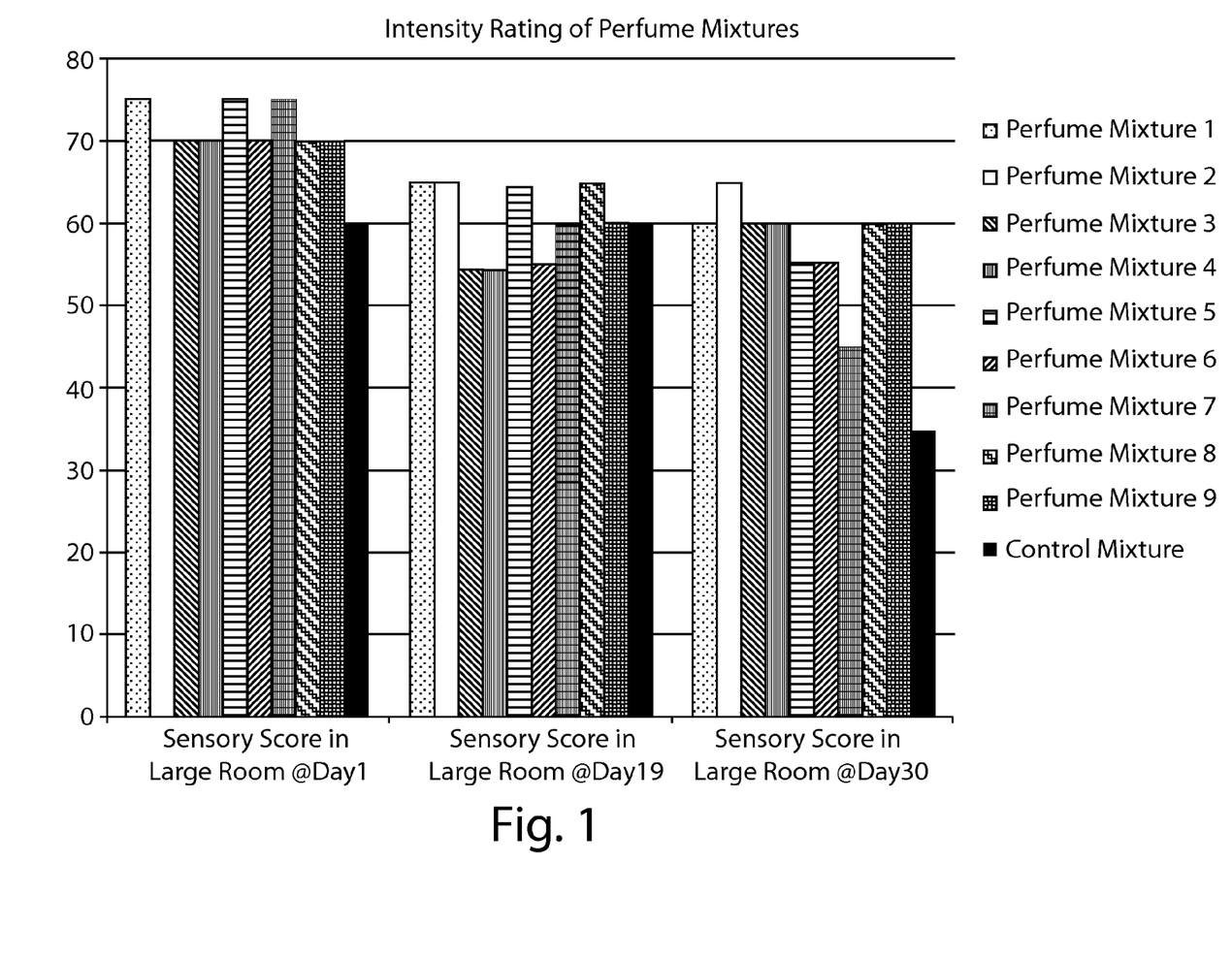
FIG. 1 is graph showing the scent intensity of various perfumes mixtures.

FIG. 1 shows that perfume mixtures according to the present invention provide surprising superior scent intensity even at Day 30.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm". All percentages and ratios are calculated by weight unless otherwise indicated.

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. An apparatus comprising:
an evaporation assistance element;
a delivery engine positioned within a housing and downstream of said evaporation assistance element, wherein said delivery engine comprises:
a reservoir containing a perfume mixture comprising an olfactive index ("OI") of at least about 12,000, wherein said perfume mixture comprises at least about 5 wt. % of perfume raw materials having an odor detection threshold ("ODT") less than or equal to about 1 ppb, and said perfume mixtures comprises about 45 wt. % to about 85 wt. % of perfume raw materials having a weighted average VP range from about 15,000 ppb to about 20,000 ppb; and
a fluid transport member;
wherein said evaporation assistance element is configured to evaporate said perfume mixture into the atmosphere.

2. The apparatus of claim 1 wherein said perfume mixture comprises an OI of at least about 25,000.

3. The apparatus of claim 1, wherein said perfume mixture comprises an OI from about 12,000 to about 100,000.

4. The apparatus of claim 1, wherein said perfume mixture comprises at least about 10 wt. % of perfume raw materials having an ODT less than or equal to about 1 ppb.

5. The apparatus of claim 1, wherein said perfume mixture comprises at least about 10 wt. % of perfume raw materials having an ODT from about 0.5 ppb to about 1 ppb.

6. The apparatus of claim 1, wherein said perfume mixture comprises about 50 wt. % to about 80 wt. % of perfume raw materials having a weighted VP range from about 15000 ppb to about 20000 ppb at 25° C.

7. The apparatus of claim 1, wherein said perfume mixture comprises about 55 wt. % to about 75 wt. % of perfume raw materials having a weighted VP range from about 15000 ppb to about 20000 ppb at 25° C.

8. The apparatus of claim 1, wherein said perfume mixture further comprises less than about 35 wt. % of a solvent.

9. The apparatus of claim 1, wherein said perfume mixture comprises less than about 20 wt. % of solvent.

10. The apparatus of claim 1 wherein said evaporation assistance element is a fan assembly configured to move a volume of air at least partially over said fluid transport member.

11. The apparatus of claim 1 wherein said fluid transport member is a microporous membrane.

12. The apparatus of claim 10 wherein said fan assembly is configured to evaporate about 15 mg/hr. to about 70 mg/hr. of said perfume mixture from said reservoir into the atmosphere.

13. The apparatus of claim 10 wherein said fan is configured to evaporate about 25 mg/hr. to about 70 mg/hr. of said perfume mixture from said fluid transport member into the atmosphere.

14. The apparatus of claim 11 wherein said microporous membrane comprises an average pore size of about 0.01 microns to about 0.03 microns.

15. The apparatus of claim 11, wherein said microporous membrane comprises an evaporative surface area of about 2 $cm^2$ to about 25 $cm^2$.

16. The apparatus of claim 1, wherein said perfume mixture comprises a surface tension of about 19 mN/m to less than about 27 mN/m.

17. A method of diffusing a perfume mixture into the atmosphere comprising the step of: providing the apparatus of claim 1.

18. The method of claim 17, further comprising the step of activating said evaporation assistance means for a duty cycle of about 5% to about 50%.

* * * * *